United States Patent [19]
Leone

[11] Patent Number: 5,488,761
[45] Date of Patent: Feb. 6, 1996

[54] FLEXIBLE SHAFT AND METHOD FOR MANUFACTURING SAME

[76] Inventor: Ronald P. Leone, 1417 York St., Mahwah, N.J. 07430

[21] Appl. No.: 282,516

[22] Filed: Jul. 28, 1994

[51] Int. Cl.⁶ .................................................. B21D 43/00
[52] U.S. Cl. ................. 29/2.25; 29/2.1; 29/173; 76/108.1; 606/80
[58] Field of Search ............................. 29/173, 2.1–2.25; 76/108.1, 108.6; 138/118; 464/57; 606/80, 81; 408/1 R; 82/1.11

[56] References Cited

U.S. PATENT DOCUMENTS

| | | | |
|---|---|---|---|
| 2,323,700 | 7/1943 | Bailey | 29/2.11 |
| 3,554,192 | 1/1972 | Isberner . | |
| 3,656,378 | 4/1972 | Davis | 29/2.25 |
| 4,362,520 | 12/1982 | Perry . | |
| 4,669,172 | 6/1987 | Petruzzi | 29/173 X |
| 4,706,659 | 11/1987 | Matthews et al. . | |
| 4,751,922 | 6/1988 | DiPietropolo . | |

FOREIGN PATENT DOCUMENTS

| | | | |
|---|---|---|---|
| 634832 | 2/1928 | France | 29/173 |
| 360740 | 11/1931 | United Kingdom | 29/173 |

*Primary Examiner*—Douglas D. Watts
*Attorney, Agent, or Firm*—Collard & Roe

[57] ABSTRACT

A shaft coupling for transmitting power including a flexible hollow rod extending in a longitudinal direction and having pairs of helical slots formed thereon. The pairs of slots are spaced from each other along the longitudinal direction of the rod. The shaft is manufactured by providing a hollow rod and advancing the rod with a combined rotational and translational motion. An opening is machined across a diameter of the rod during its advancement to form a pair of intertwined helical slots.

8 Claims, 4 Drawing Sheets

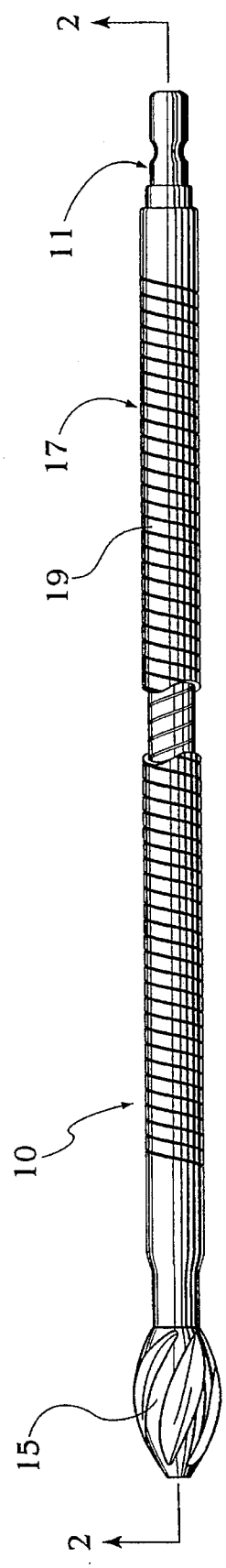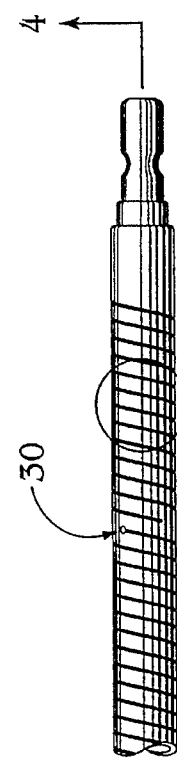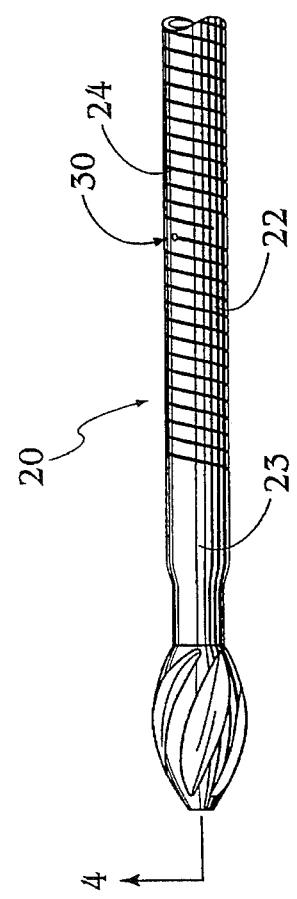
Fig.1 Prior Art
Fig.3

FLEXIBLE SHAFT AND METHOD FOR MANUFACTURING SAME

BACKGROUND OF THE INVENTION

1. Field of the Invention

The present invention relates to a flexible shaft and method for manufacturing same. More specifically, it relates to a flexible shaft that has particular application as a coupling for transmitting power, for example, in bone drills, medullary reamers, flexible bone plug introducers, and other types of flex drivers.

2. Prior Art

Various types of flexible shafts are known for a variety of applications. In the medical field of orthopedics, medullary reamers are used to enlarge the medullary canals of bone in preparation for the insertion of fixation devices, performing an intramedullary osteotomy, stimulating bone growth, the insertion of a plug to preclude bone cement from migrating while it is in its viscous state, and for other reasons. The medullary canals of bone are seldom straight. More typically, the canal will have some degree of curvature to it. Should a straight and rigid series of reamers be employed to enlarge the canal, there is considerable likelihood that the reamer, in not being capable of following the bone's curvature, will not remove the desired uniform amount of bone tissue. In such a situation, excession tissue removal occurring in at least one plane will be experienced as the reamer is advanced. For this reason, medullary canals are almost always prepared with reamers having a flexible shaft.

These flexible medullary reamers consist of spiral or helically wound metal wire(s) or strip(s), which comprise the shaft of the reamer. A disadvantage of this design is that these reamers can be operated only in the forward or clockwise mode of rotation. If operated in the reverse or counter-clockwise mode, which occasionally is required to free a lodged reamer and to facilitate normal removal, the shaft unwinds, thus rendering the reamer permanently deformed, unusable, and unrepairable. This adds considerably to the cost of maintaining a serviceable set of medullary reamers. Further, a lodged cutting head may subsequently be extremely difficult, if not impossible to remove without further violation of the involved bone and surrounding tissues.

Another disadvantage of said design is the extreme difficulty in their proper and thorough cleaning after use. The spiral or helically wound metal shafts contain many voids of various sizes. Blood and tissue readily infiltrate such voids and become trapped within the confines of the shaft. When the reamer is in use, the voids are considerably distorted and enlarged as the reamer is advance towards and within the medullary canal, thus providing ready access for the particles of tissue. Prior to use, all medullary reamers are sterilized and hopefully, the blood and tissue particles not evacuated during the cleaning process and remaining within the interstices of the reamers, are at least rendered harmless. However, depending upon the amount and composition of the extraneous particles and their degree of isolation from the sterilizing process, said particles may not be rendered sterile. Even in a sterile condition, these foreign particles may still cause problems of infection should they become dislodged from the confines of the reamer and come into contact with the patient's internal tissues. Medical professionals recognize this problem but acquiesce to using these reamers for lack of an acceptable alternative.

A further disadvantage of this medullary reamer is that the torsional load it is subject to when in use results in poor power transfer and varying degrees of distortion of said shaft. If the power source providing the rotational energy to the reamer is great enough, said coils may tighten sufficiently to adversely affect the intended flexibility of the shaft. Another disadvantage associated with a spiral or helically wound reamer is the trauma it imposes to surrounding tissues. This results when the shaft of the reamer is not completely within the medullary canal as would occur during the initial reaming process. As the shaft rotates, that portion remaining outside of the medullary canal can become excessively flexed and distorted, thus enlarging the voids between the coils of the shaft. As the flexed shaft rotates, tissue lying outside of the canal and unintended for removal, becomes trapped within the voids and are torn from their underlying structures.

SUMMARY OF THE INVENTION

In is therefore an object of the present invention to overcome the drawbacks of the prior art and to provide a flexible shaft which operates as an efficient coupling for transmitting power and which can be rotated in both directions.

It is a further object of the present invention to provide a medullary reamer shaft which can be easily and effectively cleaned between cases.

It is a further object of the present invention to provide a method for manufacturing a flexible shaft from a variety of materials, whereby the strength and flexibility of the shaft can be,, controlled during the manufacturing process.

These and other related objects are achieved according to the invention by a shaft coupling for transmitting power, including a flexible hollow rod extending in a longitudinal direction and having pairs of helical slots formed thereon. The pairs of slots are spaced from each other along the longitudinal direction of the rod. Each pair of slots consists of a first helical slot intertwined with a second helical slot. Each slot has the same length extending along the longitudinal direction of the rod. Both slots extend along the longitudinal direction to the same extent, i.e., they begin and end at the same point along the longitudinal direction. In other words, both slots are completely disposed within a single region.

In a specific application, the objects of the invention are achieved by a medullary rotational reamer for clearing, enlarging or otherwise modifying the medullary space of bones. The reamer includes a flexible shaft with a cutting head at one end and an adapter piece at its opposite end for connecting the shaft to a rotational drive element thereby causing rotation of the shaft. The flexible shaft consists of a hollow rod extending in a longitudinal direction and having a plurality of pairs of helical slots formed thereon. The pairs of slots are spaced from each other along the longitudinal direction of the rod. A plurality of continuous surfaces are also formed on the rod. Each surface extends circumferentially around the rod and is located between adjacent spaced pairs of slots to form a helical slot interruption. The shaft, the cutting head and the adapter piece are integrally formed and made from a material selected from the group consisting of stainless steel, titanium, chrome cobalt molybdenum alloy, a carbon fiber composite, or any suitable material.

Each pair of slots includes a first slot having a first series of points and a second slot having a second corresponding series of points. The corresponding point from the first and second slots are disposed diametrically opposite each other on the hollow rod.

The method of manufacturing a flexible shaft according to the invention includes the following steps. Initially, a hollow rod is provided that extends in a longitudinal direction. The hollow rod is rotated around its longitudinal central axis and moved along in the longitudinal direction. An opening is machined across a diameter of the rods during the step of rotating and moving to form a pair of intertwined helical slots. The rate of rotation of the hollow rod is adjustable with respect to movement along the longitudinal direction to control the pitch of the helical slots. The hollow rod is made from a material selected from the group consisting of stainless steel, titanium, chrome cobalt molybdenum alloy, a carbon fiber composite, or any suitable material.

The step of machining includes one of wire electrical discharge machining, water jet machining, laser machining, spark erosion machining, and rotary cutting machining. The step of machining further includes machining for a predetermined period of time to form a pair of slots having end points. The rod is then advanced to form a continuous surface devoid of slots adjacent one of the end points. The steps of machining and advancing are repeated to form a plurality of slots separated by continuous surfaces.

Each of the continuous surfaces extends circumferentially around the rod to form a helical slot interruption. A cutting head and adapter piece are machined onto opposite ends of the rod, or connected on by welding or other suitable means. The shaft, the cutting head and the adapter piece are electropolished for medical applications. The shaft is cleaned by inserting a brush or cannulated tube into the hollow rod. Pressurized water is forced through the cannulated tube, against an inner surface of the hollow rod, and through the slots to clean the shaft. Pressurized water may also be sprayed on the external surface of the rod to clean it.

BRIEF DESCRIPTION OF THE DRAWINGS

Other objects and features of the present invention will become apparent from the following detailed description considered in connection with the accompanying drawings, which disclose a single embodiment of the present invention. It should be understood, however, that the drawings are designed for the purpose of illustration only and not as a definition of the limits of the invention.

In the drawings, wherein similar reference characters denote similar elements throughout the several views:

FIG. 1 is a side elevational view, in part cross section, of a prior art reamer showing the inner shaft;

FIG. 3 is a side elevational view of an embodiment of a reamer according to the present invention;

DETAILED DESCRIPTION OF PREFERRED EMBODIMENT

Figure 2:
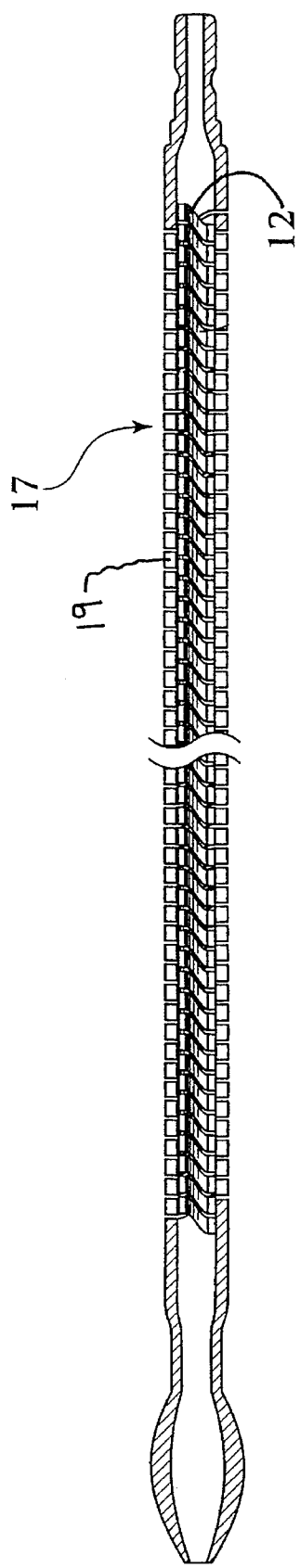
FIG. 2 is a cross-sectional view of the prior art reamer taken along the line 2—2 from FIG. 1.

Referring now in detail to the drawings, and in particular FIG. 1, there is shown a prior art reamer 10 having a connection member 11 provided for attachment to a drive means such as an electric motor. At the other end of reamer 10, a drill bit 15 is provided so as to enable drilling of an intramedullary canal. Connecting bit 15 and connection means 11 is an elongated shaft 17 which is made of a long strip of metal wound in a spiral-like fashion to form coils 19 which extend throughout the longitudinal extent of shaft 17. Shaft 17 has not been found to be an effective means of transmitting torque from connection means 11 to drill bit 15, particularly when drill bit 15 encounters an obstruction tending to stop its motion. Shaft 17 by virtue of its coil-like construction, allows connection means 11 to be rotated by the drive motor with respect to bit 15, thereby enabling energy to be stored up therein. When the energy stored up in shaft 17 exceeds the forces which are retaining bit 15 in a stationary position, bit 15 will then jump forward. In some cases, this may cause damage to the structure of the bone or surrounding tissue.

A further disadvantage of the prior art reamer is evident when bit 15 encounters an obstruction which is not easily removed. The surgeon operating reamer 10 may be tempted to reverse the direction of operation thereof, to loosen bit 15 from the obstruction. If this is done, and bit 15 is not removed from the obstruction thereby, the reversal of the motion of the drive motor will cause shaft 17 to uncoil. This not only irreparably damages shaft 17 but also increases the potential for the damage to the surrounding bone tissue. In a further aspect, if sufficient reverse motion of connection means 11 is made with respect to bit 15, shaft 17 may become sufficiently widened so as to prevent its extraction from the opening formed by bit 15. Accordingly, several disadvantages in the prior art reamer 10 are self-evident.

A further disadvantage of the prior art reamer stems from the fact that a second inner coil 12 is disposed within shaft 17, as can be seen in FIG. 2. As coil 19 and inner coil 12 flex during use, the gaps within the coil are alternately opened and closed which allow foreign particles to penetrate into both coils. Since there is no way to clean the surfaces between inner coil 12 and coil 19, foreign particles may remain lodged within shaft 17.

Figure 4:
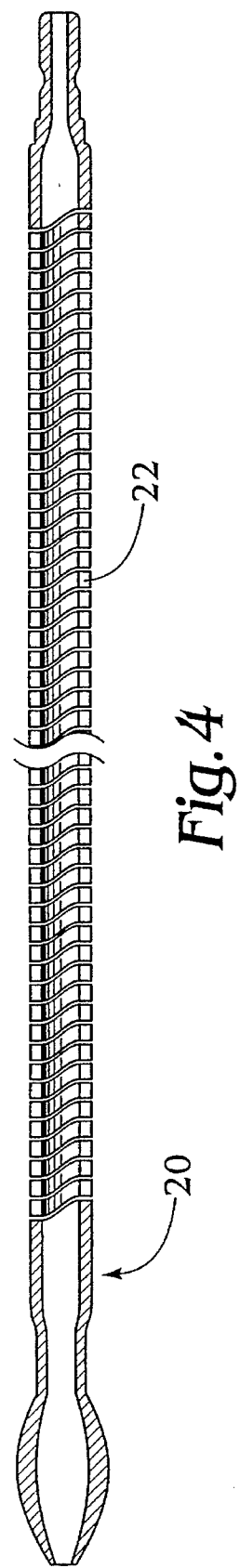
FIG. 4 is a cross-sectional view of the reamer according to the invention taken along the line 4—4 from FIG. 3.
Figure 5:
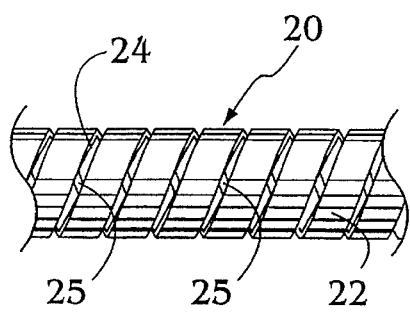
FIG. 5 is an enlarged side elevational view of the reamer shaft.

As can be seen in FIGS. 3, 4 and 5, reamer 20, according to the invention, consists of a single coil 22. Coil 22 is made from pairs of helical slots 24 which are machined into a shaft 23, in a manner that will be described more fully below. Along the length of shaft 20, helical slot interruptions 30 are formed which consist of a continuous surface extending circumferentially around shaft 23. Helical slot interruptions 30 provide added strength to shaft 23 and as a result reamer 20 does not require an inner coil.

In addition, slots 24 may be machined wider than with the prior art devices such that, as can be seen in FIG. 5, regions 25 exist where it is possible to look completely through shaft 23 by aligning slots on the front side of the shaft with slots on the rear side of the shaft. The strength and flex characteristics of shaft 23 may be adjusted by controlling the pitch and width of slots 24.

In addition, the position and number of helical slot interruptions 30 can affect the strength characteristics of shaft 23. Typically, along a 20" shaft, three helical slot interruptions 30 are spaced evenly along the length of shaft 23. This divides slots 24 into four sets of slots of equal length. The hollow interior of reamer 20 may accommodate an insert to stiffen the shaft, a guide pin which was previously positioned within the bones medullary space to pre-flex the shaft, or cleaning equipment.

Figure 6:
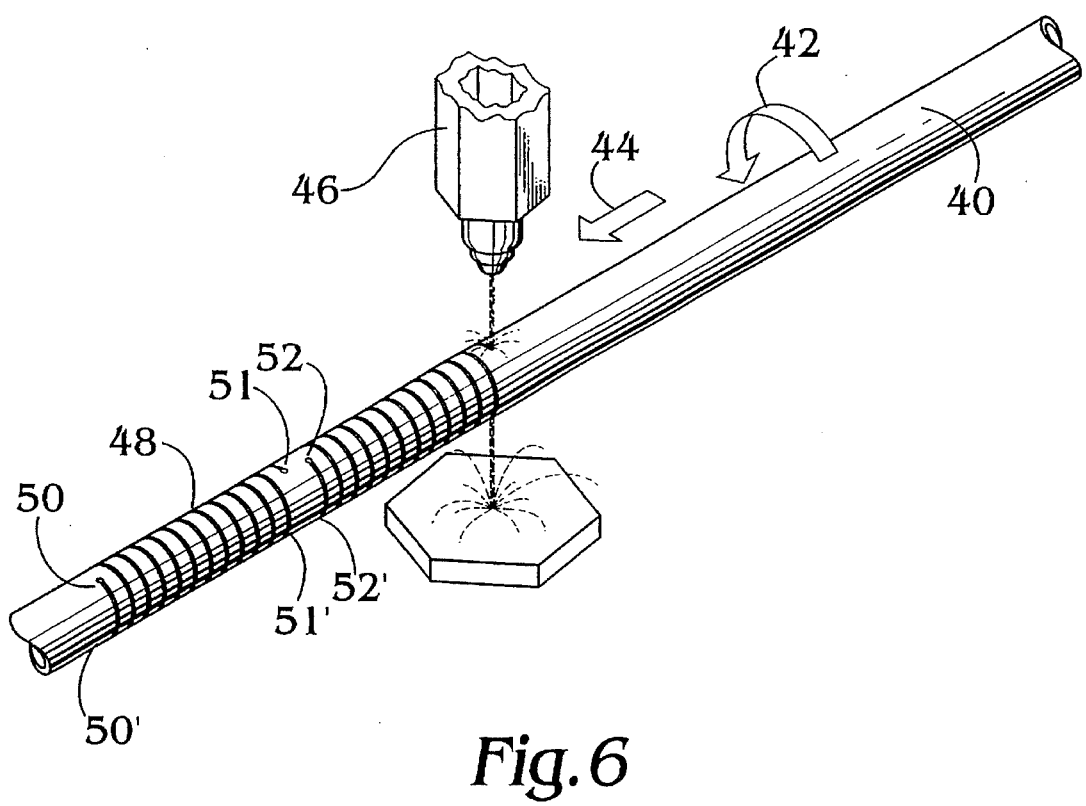
FIG. 6 is a perspective view showing the reamer shaft being advanced as it is machined.

FIG. 6 shows a method for manufacturing shaft 23. Initially, a hollow rod 40 is provided which can be made, for example, from stainless steel, titanium, chrome cobalt molybdenum, a carbon fiber composite, or any other suitable spring material. Rod 40 is advanced along a helical path by a combination of rotational motion 42 and translational motion 44. A machine head 46 is oriented so as to machine an opening across a diameter of rod 40. When machine head 46 begins machining, a first helical slot begins at point 50 and a second corresponding helical slot begins at point 50', diametrically opposed to point 50. As rod 40 advances, a pair of intertwined helical slots are formed thereon. At point 51 and diametrically opposite point 51', machining is terminated. Rod 40 continues to advance, for example, ¼, ½ or ¾ of a turn At points 52 and 52' machining resumes and a second pair of intertwined helical slots are formed along rod 40.

As can be appreciated, the pitch of helical slots 48 can be adjusted by changing the rate of rotational motion 42 with respect to the rate of translational motion 44. The speed at which slots 48 are machined is determined by the capacity of machine head 46. Shafts of a commercially acceptable quality have been machined by wire electrical discharge machining. However, helical slots 48 may also be machined by electrical discharge machining, water jet machining, laser machining or spark erosion machining.

In the manufacture of medullary reamers, the cutting head and adapter piece may be machined onto the ends of rod 40 to form a reamer of unitary construction. A distinct advantage with this method of manufacturing is that additional time, which would otherwise be required to weld or otherwise connect the adapter and cutting head to the rod is avoided. In addition, a reamer of unitary construction may undergo electro-polishing which is a chemical treatment to polish the material and give it a smooth polished finish. The polished surface resists contamination from foreign particles and is easier to clean. Electro-polishing cannot easily be carried out on a structure consisting of several overlapping connected parts.

Figure 7:
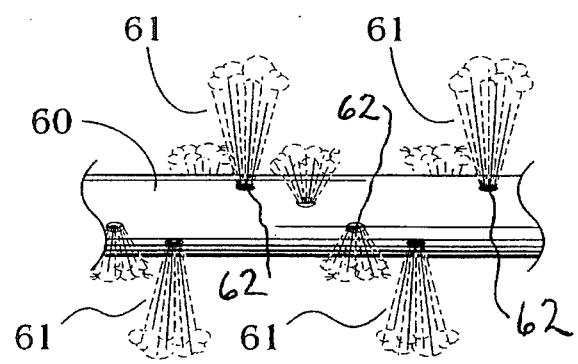
FIG. 7 is a fragmentary side elevational view of a cannulated tube used for cleaning the reamer shaft.

In addition to the wide slots and hollow interior shown in FIG. 5, and in addition to the electro-polishing described above, reamer 20 may be further effectively cleaned by a cannulated tube 60 shown in FIG. 7. This tube is configured and dimensioned to slide within shaft 20. Pressurized water 61 or other cleaning fluid is forced through apertures 62 to clean the inside of shaft 23 as well as the opposed surfaces forming the slots. Because slots 24, as can be seen in FIG. 5, are generally wider than the prior art slots, they can be effectively cleaned by a pressurized fluid.

As was mentioned earlier, rods of a variety of material may be machined according to the disclosed process to provide a variety of operating characteristics. The configuration and length of the helical slot may be combined with helical slot interruptions of varying configurations to provide a wide range of flexible shafts which are extremely strong and easily cleaned. The primary advantage of having the helical slot interruptions is that the shaft can be rotated in both directions. In other words, if the shaft is configured as a medullary reamer, the surgeon has all of the advantages attendant with the prior art reamers, but additionally has the ability to operate the reamer shaft according to the invention in a reverse or counterclockwise direction. The helical slot interruptions effectively prevent the coil from unravelling which is a serious problem where the helical slot extends uninterrupted along the entire length of the shaft.

While only a single embodiment of the present invention has been shown and described, it is to be understood that many changes and modifications may be made thereunto without departing from the spirit and scope of the invention as defined in the appended claims.

What is claimed is:

1. A method of manufacturing a flexible shaft coupling comprising the steps of:

providing a hollow rod with a longitudinal central axis;

rotating said hollow rod around its longitudinal central axis, and moving said hollow rod in an axial direction; and machining an opening across a diameter of said rod during said step of rotating and moving to form a pair of intertwined helical slots.

2. The method according to claim 1, wherein the speed of rotation of said hollow rod is adjustable with respect to axial movement of said hollow rod to control the pitch of said helical slots.

3. The method according to claim 2, wherein said hollow rod is made from a material selected from the group consisting of stainless steel, titanium, chrome cobalt molybdenum and a carbon fiber composite.

4. The method according to claim 3, wherein said step of machining comprises one of wire electrical discharge machining, water-jet machining, laser machining, spark erosion machining and rotary cutting machining.

5. The method according to claim 4, wherein said step of machining comprises:

machining for a predetermined period of time to form a pair of slots having endpoints;

advancing said rod to form a continuous surface devoid of slots adjacent one of said endpoints; and repeating said steps of machining and advancing to form a plurality of pairs of slots separated by continuous surfaces.

6. The method according to claim 5, wherein each of said continuous surfaces extends circumferentially around said rod to form a helical slot interruption.

7. The method according to claim 6, further comprising the steps of:

machining a cutting head and an adaptor piece on opposite ends of said rod; and electro-polishing said shaft, said cutting head and said adaptor piece.

8. The method according to claim 7, further comprising the steps of:

providing a cannulated tube for inserting into said hollow rod; and forcing a pressurized fluid through said cannulated tube against an inner surface of said hollow rod and through said slots to clean said shaft.

* * * * *